United States Patent [19]

Shinkai et al.

[11] Patent Number: 5,099,033

[45] Date of Patent: Mar. 24, 1992

[54] PROCESS OF MAKING 2,5-DIARYL TETRAHYDROFURANS AND ANALOGS THEREOF USEFUL AS PAF ANTAGONISTS

[75] Inventors: Ichiro Shinkai, Westfield; Andrew S. Thompson, Mountainside; Thomas R. Verhoeven, Watchung, all of N.J.

[73] Assignee: Merck & Co., Inc., Rahway, N.J.

[21] Appl. No.: 546,487

[22] Filed: Jun. 29, 1990

[51] Int. Cl.$^5$ .................. C07D 307/02; C07D 498/00
[52] U.S. Cl. .................... 549/218; 549/222; 549/475; 549/496; 549/497; 549/498; 549/499; 549/500; 549/501; 549/502; 549/504
[58] Field of Search ............... 549/502, 497, 496, 218, 549/501, 475, 491, 498, 499, 500, 504, 222

[56] References Cited

U.S. PATENT DOCUMENTS

| | | | |
|---|---|---|---|
| 2,873,275 | 2/1959 | Ramsden | 549/497 |
| 2,921,940 | 1/1960 | Ramsden | 549/497 |
| 4,539,332 | 9/1985 | Biftu | 514/461 |
| 4,772,752 | 9/1988 | Brown | 568/6 |
| 4,866,181 | 9/1989 | Brown | 546/348 |

FOREIGN PATENT DOCUMENTS

| | | |
|---|---|---|
| 0199324 | 10/1986 | European Pat. Off. |
| 0305180 | 3/1989 | European Pat. Off. |
| 0322033 | 6/1989 | European Pat. Off. |

OTHER PUBLICATIONS

J. W. Gillard and M. Israel, Tetrahedron Letters, 1981, 22, 513.
E. J. Corey, et al., J. Am. Chem. Soc. 1987, 109, 7925.
M. M. Ponpipom, et al., Tetrahedron Letters, 1988, 29, 6211.
M. M. Ponpipom, et al, Biochem. & Biophys. Res. Com. 150, 1213 (1988).
H. C. Brown, et al., J. Am. Chem. Soc. 1988, 110, 1539.
H. Stetter, et al., Agnew. Chem. Int. Ed. Eng. 85, 89 (1973) & German equivalent H. Stetter, et al., Agnew. Chem. Int. Ed. Eng. 12, 81 (1973).

*Primary Examiner*—C. Warren Ivy
*Assistant Examiner*—Raymond Covington
*Attorney, Agent, or Firm*—Curtis C. Panzer; Hesna J. Pfeiffer

[57] ABSTRACT

The present invention is directed to a process of making tetrahydrofuran of the formula (D)

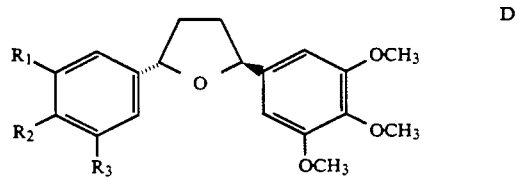

resulting in 2,5-diaryltetrahydrofuran PAF antagonists of pharmaceutically acceptable purity.

19 Claims, No Drawings

PROCESS OF MAKING 2,5-DIARYL TETRAHYDROFURANS AND ANALOGS THEREOF USEFUL AS PAF ANTAGONISTS

BACKGROUND OF THE INVENTION

Compounds of formula (D) are known and are known to possess utility as platelet-activating factor (PAF) antagonists

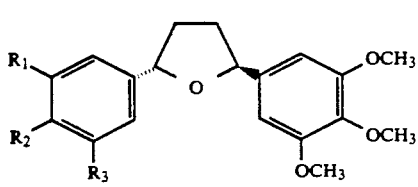

D

Platelet-activating factor (PAF) has recently been identified as an acetyl glyceryl ether phosphorylcholine (AGEPC), i.e., 1-O-hexadecyl/octadecyl-2acetyl-sn-glyceryl-3-phosphoc holione (Hanahan D. J., etal., *J. Biol. Chem.* 225:5514, 1980). PAF has been linked to various biological activities and pathways making it one of the important mediators responsible for a variety of physiological processes including activation or coagulation of platelets, pathogenesis of immune complex deposition, smooth muscle contraction, inflammation, hypotension, shock, pain, edema as well as respiratory, cardiovascular and intravascular alterations. These physiological processes are in turn associated with a large group of diseases, for example, inflammatory disease, cardiovascular disorder, hypotension, shock, psoriasis, allergic and skin diseases, asthma, lung edema, peptic or stomach ulcer, dental pain, and adult respiratory distress syndrome.

Some compounds of formula (D) as well as their utility as PAF antagonists and their method of preparation are disclosed in U.S. Pat. No. 4,539,335 which issued on Sept. 3, 1985; E. P. 0 199 324, which published on Oct. 29, 1986; E. P. 0 322 033, published on June 28, 1986copending U.S. application Ser. Nos. 362,919, filed June 8, 1989 and 505,712 filed Apr. 11, 1990 all of which are hereby incorporated by reference.

Preparation of compounds of formula (D) is achieved via an acid catalyzed cyclization of a 1,4-diaryl-1,4-butanediol. This method, however, produces an isomeric mixture of cis and trans 2,5-diaryl tetrahydrofurans. See *Tetrahedron Letters*, 29, p. 6211 (1988). In contrast, the optically pure 5-aryl-butyro-lactones of the present invention are readily converted in a stereoselective reaction to a single physiologically active trans-isomer.

Some 2,5-diaryltetrahydrofurans have been prepared from 5-aryl substituted furanosides via a direct lactol activation with TMS-Br followed by coupling with an organometallic partner. See *J. Am. Chem. Soc.*, 109, p. 7925 (1987). However, this method, when applied to electron-rich aromatic ring systems such as 3,4,5-trimethoxyphenol, produces low yields and is accompanied by significant side products.

Preparation of a furanosyl bromide from a furanosyl acetate with trimethylsilyl bromide has also been described. See *Tetrahedron Letters*, p. 513 (1981). Unfortunately, it is our experience that this technique leads to incomplete bromination with a consequent loss of yield and purity in the subsequent coupling reaction.

In contrast to the prior art, the instant process provides an efficient means to produce optically pure trans-2,5-diaryltetrahydrofurans from optically pure 5-aryl-γ-butylrolactones in high yield with high stereoselectivity (trans:cis greater than 75:1) and high degrees of regiocontrol with respect to substitution on the aromatic ring.

Accordingly, the present invention is directed to the preparation of the most potent isomers of known or novel tetrahydrofuran derivatives as PAF antagonists and use them for the treatment of various diseases including prevention of platelet aggregation, hypotension, inflammation, asthma, lung edema, adult respiratory distress syndrome, various shock syndromes, cardiovascular disorders and other related skeletal-muscular disorders, graft-host rejection, nephritis, pancreatitis and lupus.

BRIEF DESCRIPTION OF THE INVENTION

The present invention is directed to a process for converting optically pure 5-aryl-γ-butylrolactone, Compound A,

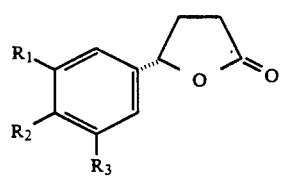

A to optically pure trans-2,5-diaryltetrahydrofuran, Compound D

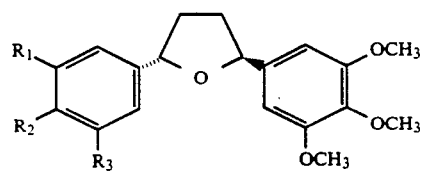

D

The process involves a four step sequence in which the 5-aryl-γ-butylrolactone is activated through its conversion to a glycosyl bromide. The activated bromide is coupled in a stereoselective manner with an aryl metal species to establish the trans-2,5 substitution pattern about the tetrahydrofuran ring.

DETAILED DESCRIPTION OF THE INVENTION

The present invention is directed to a process of making 2,5-diaryltetrahydrofuran PAF antagonists of pharmaceutically aceptable purity of the following structural formula:

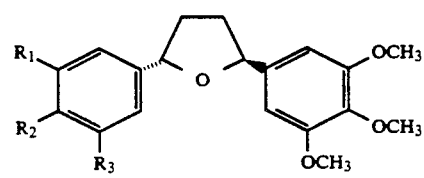

wherein:

$R^1$ is iodide, or bromide, or $R^1$ is $S(O)_nR_a$ in which n is 0, 1 or 2 and $R_a$ is selected from the group consisting of
(a) $C_{1-6}$alkyl,
(b) $C_{2-6}$alkenyl,
(c) $C_{2-6}$alkynyl,
(d) substituted $C_{1-6}$alkyl wherein the substituent is selected from the group consisting of hydroxy, protected hydroxy, N-Cl-4alkylamino, and N,N-Cl-4di-alkylamino,
(e) $C_{1-6}$alkoxy-$C_{1-6}$alkyl,
(f) $C_{1-6}$alkylcarbonyl-$C_{1-6}$alkyl; and $R_2$ is selected from the group consisting of
(a) $C_{1-12}$alkoxy,
(b) $C_{2-6}$alkenyloxy,
(c) $C_{2-6}$alkynyloxy,
(d) $C_{2-6}$(halo)x alkoxy wherein x ius 1,2,3,4 or 5 and halo is chloro fluoro or bromo,
(e) substituted $C_{1-6}$alkoxy wherein the substituent is hydroxy, or protected hydroxy,
(f) $C_{1-6}$alkoxy-$C_{1-6}$alkoxy,
(g) $C_{1-6}$alkyl $S(O)_m$-$C_{1-6}$alkoxy in which m is 0, 1 or 2,
(h) $C_{1-6}$alkyloxysulfonyl-$C_{1-6}$alkoxy,
(i) $C_{1-6}$alkyl carbonyl-$C_{1-6}$alkoxy,
(j) phenyl-$C_{1-6}$alkoxy,
(k) azido-$C_{1-6}$-alkoxy,
(l) cyano-$C_{1-6}$alkoxy,
(m) $C_{1-6}$alkylS(O)$_m$-$C_{1-6}$alkoxy,
(n) N-substituted, or N,N-disubstituted amino-$C_{1-6}$alkyloxy wherein the substituents are each individually $C_{1-6}$alkyl;

$R_3$ is selected from the group consisting of
(a) $C_{1-6}$alkoxy,
(b) substituted $C_{1-6}$alkoxy wherein the substituent is selected from the group consisting of hydroxy, protected hydroxy, N—$C_{1-4}$alkylamnio, N,N-di$C_{1-4}$alkylamino,
(c) —O—$C_{1-6}$alkyl—O—$R^{10}$, wherein $R^{10}$ is
 (1) —$PO_2(OH)^-$ $M^+$ wherein $M^+$ is a pharmaceutically acceptable cation,
 (2) —$C(O)(CH_2)_2$—$CO_2^-M^+$, or
 (3) —$SO_3^-M^+$,
(d) $C_{1-6}$-alkylcarbonyl-$C_{1-6}$alkoxy,
(e) $C_{1-6}$-alkoxyaminocarbonyloxy,
(f) halophenyl$C_{1-6}$-alkoxy, and
(g) $C_{1-6}$carboxyalkoxy.

As is appreciated by those of ordinary skill in the art are groups suitable for protecting the hydroxyl groups include trialkyl silyl, acetate, benzoate, and ether protection. See also Protective Groups in Organic Synthesis, Theodora W. Green, John Wiley and Sons 1981.

The process is outlined in Scheme 1 and comprises four steps.

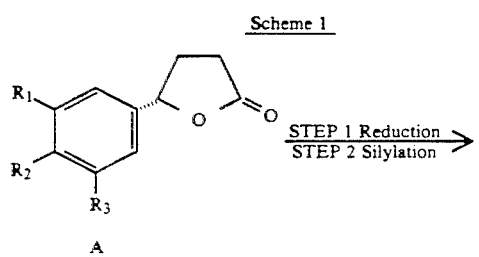

A

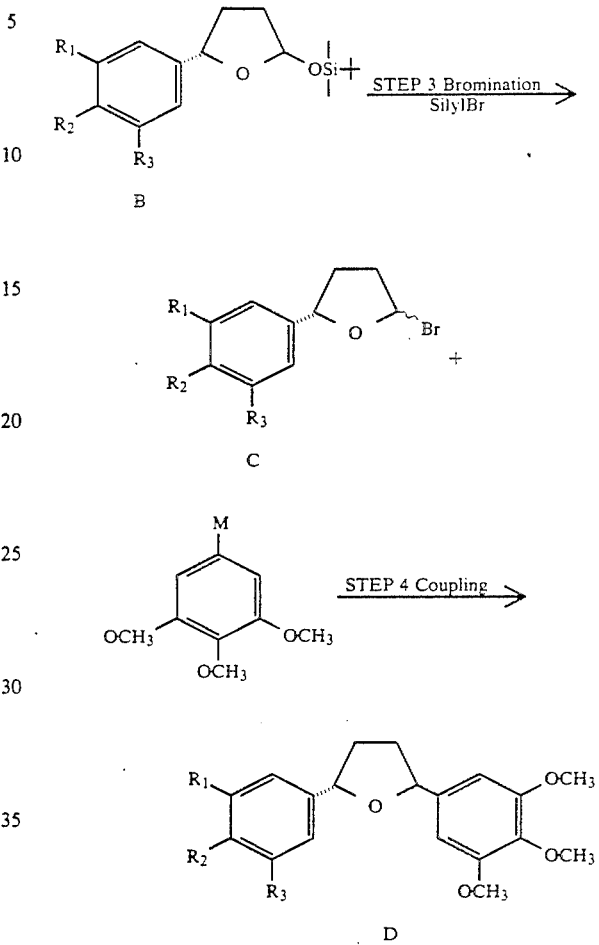

As shown in Scheme 1, butylrolactone, Compound A, is reduced to a lactol, then silylated, providing sily-lactol, Compound B. Compound B is then activated through treatment with silylbromide, forming a glycosyl bromide Compound C. Coupling is subsequently achieved using an aryl copper species to stereoselectively produce the target trans-2,5-diaryltetrahydrofuran, Compound D.

In one embodiment, the invention concerns a process of making compounds of the formula D, comprising:

(A) contacting of a compound of the formula

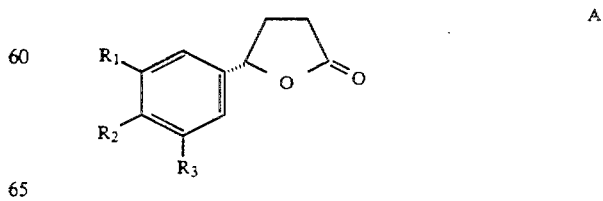

A in an aromatic solvent with a reducing agent to yield compound A';

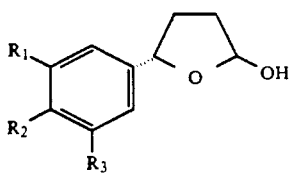

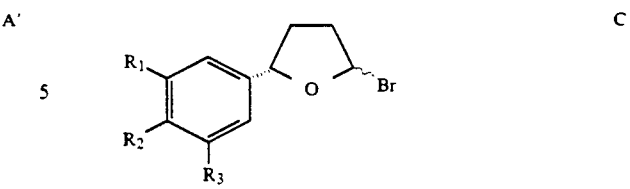

wherein the hydroxyl groups of substituent $R_1$, $R_2$ and $R_3$ are protected.

For purposes of the specification, the third solvent includes but is not limited to etheral solvents such as diethyl ether di-n-butyl and diisopentyl ethers, anisole, cyclic ethers such as tetrahydorpyran, 4-methyl-1,3-dioxane, tetrahydrofurfuryl methyl ether, ethyl ether, furan and tetrahydrofuran, or halocarbon solvents such as mono or di halo $C_{1-4}$alkyl including methylene chloride. Methylene chloride is preferred. The silyl bromide includes, but is not limited to tri $C_{1-6}$ alkylsilyl bromide with trimethylsilylbromide preferred for complete reaction. The molar ratio of silyl bromide to compound B should be 1 to or greater, preferably 1.1–1.3 to 1. The reaction is allowed to proceed until essentially complete in about 0.5 to 3 hours, typically 1.5 hrs.

The reaction temperature is approximately −70° to −10° C., preferably −60° C.

While the reaction can be carried out at up to 100 atmospheres of pressure, the reaction is preferably carried at under ambient pressure. The presence of oxygen is preferably minimized, such as by use of a nitrogen or other inert atmosphere.

For purposes of the specification, aromatic solvents include, but are not limited to, benezene, toluene and xylene, preferably toluene. Reducing agents include, but are not limited to metal hydrides such as sodium bis-methoxy, ethoxy aluminum hydride and diisobutylaluminum hydride preferably, diisobutylaluminium hydride. For complete reaction the molar ratio of reducing agents to lactone should be approximately 1 to 1, or larger; preferably 1.25 to 1. The reaction may be conducted from −80° C. to −50° C., preferably −75° C. to −60° C. The reaction is allowed to proceed until substantially complete in about 1 to 2 hours, typically 1.25 or 1.5 hours. The reaction can then be quenched by addition of $C_{1-6}$alkanol such as methanol.

While the reaction can be carried out at up to 100 atmospheres of pressure, the reaction is preferably carried at under ambient pressure;

(B) contacting of compound A' with a tri $C_{1-6}$alkyl chlorosilane in a second solvent and a base to yield the silyllactol Compound B;

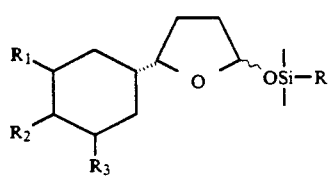

wherein R is $C_{1-6}$ alkyl;

For purposes of this specification tri-$C_{1-6}$alkylchlorosilanes include but are not limited to tri-$C_{1-6}$ alkyl chlorosilane wherein each alkyl group is independently defined as $C_{1-6}$ alkyl. Preferred is tert-butyldimethylchlorosilane. The second solvent includes, but is not limited to N,N-di$C_{1-6}$alkyl carbonyl amide, such as N,N-dimethyl formamide (DMF) or toluene, tetrahydrofuron (THf), dichloromethane or other non-protic solvent; DMF is preferred. Nitrogen containing bases include but are not limited to pyrrole, pyridene, pyrrolidine tri $C_{1-3}$alkyl amino such as triethyl amine and imidazole. Imidazole is preferred for complete reaction. The molar ratio of base to compound A' should be approximately 2 to 1 or greater. A ratio of 2.2 to 1 is typical. The ratio of silane to compound A is approximately 1.1 to 1 up to 2.5 to 1; preferably 1 to 1. The reaction should be allowed to proceed until complete in approximately 1 to 3 hrs. The reaction temperature may be 0° to 80° C., preferably 25°–30° C.

While the reaction can be carried out at up to 100 atmospheres of pressure, the reaction is preferably carried at under ambient pressure. The presence of oxygen is preferably minimized, such as by use of a nitrogen or other inert atmosphere.

(C) Contacting of Compound B with a silyl bromide in a third solvent to yield a glycosyl bromide Compound C;

(D) Contacting of Compound C with an organo metallic reagent species of the formula

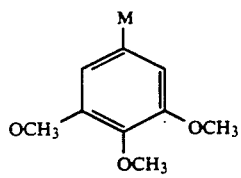

wherein M is magnesium, aluminum, zinc, copper or lithium in a fourth solvent to yield a compound of formula D;

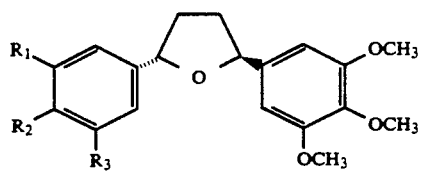

For purposes of this specification the fourth solvent includes, but is not limited to ethers as broadly defined above; preferably THF. The organo metallic reagent includes, but is not limited to those derived from aryl Grinard reagents such as 3,4,5-trimethoxy phenylmagnesium bromide in the presence of a copper salt such as copper cyanide or dilithium tetrachlorocuprate. The ratio of organometallic reagent to compound C is approximately 1–1.5 to 1, preferably 1.4 to 1. The reaction is allowed to proceed until essentially complete in about 0.5 to 3. hours. Typically 1.0 hours. The reaction temperature is approximately −70° to −10° C., preferably −60° C.

While the reaction can be carried out at up to 100 atmospheres of pressure, the reaction is preferably carried at under ambient pressure. The presence of oxygen is preferably minimized, such as by use of a nitrogen or other inert atmosphere.

This invention further concerns a process of making compounds of formula D wherein:

$R_1$ is I, $R_2$, is $OCH_2CH_2CH_3$ and $R_3 = CH_3O$;

$R_1 = I$; and $R_3$ is O $(CH_2)_3$—O—$PO_3H_2$, $R_2$, is $OCH_2CH_2CH_3$ and $R_1 = I$; $(CH_2)_3$—OH, $R_2$, is $OCH_2CH_2CH_3$ and $R_3$ is $CH_3O$.

The resulting compound of Formula D can be converted to optically pure (−)-(2S,5S)-2-(3(2-hydroxyethylsulfonyl)-4-(n-propoxy)-5-methoxyphenyl)-5-(3,4,5-trimethoxyphenyl)tetrahydrofuran, a potent PAF antagonist.

Additional optically pure PAF antagonists that can be produced include (−)-(2S,5S)-2-(3-(2-oxopropylsulfonyl)-4-(n-propoxy)-5-(3-phosphopropoxy) phenyl-5-(3,4,5-trimethoxyphenyl)-tetrahydrofuran; (−)-(2S,5S)-2-(3-(2-oxopropylsulfonyl)-4-(n-propoxy)-5-(3-hydroxypropoxy)phenyl-5-(3,4,5-trimethoxyphenyl)tetrahydrofuran; and (−)-(2S,5S)-2-(3-(2-hydroxyopropylsulfonyl)-4-(n-propoxy)-5-(3-hydroxypropoxy)phenyl-5-(3,4,5-trimethoxyphenyl)tetrahydrofuran.

The compound of Formula A may be prepared according to the method of Corey et. al., *J. Am. Chem. Soc.*, (1987), 109, 7925. Preferably they are prepared as outlined in Scheme 2 and described in greater detail thereafter.

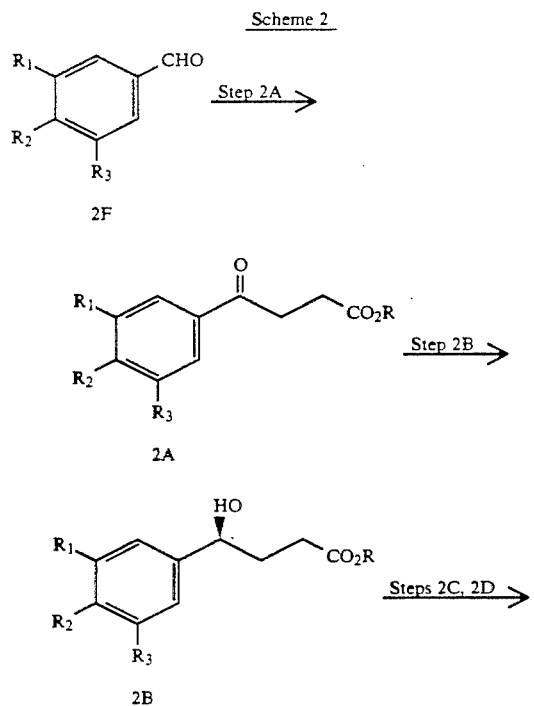

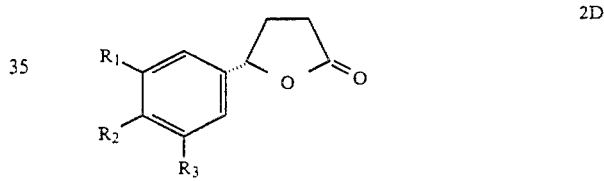

In step 2A an in situ prepared acyl anion equivalent, compound 2F, which is derived from a substituted benzaldehyde is chemoselectively added to an α,β-unsaturated ester, to yield Compund 2A. This single transformation assembles the requisite carbon framework from commercially available precursors. In step 2B an enantioselective reduction utilizes β-chlorodiisopinocampheyl borane in an unprecedented manner to produce an optically enriched 4-aryl-4-hydroxy-butanoate, Compound 2B. In steps 2C to 2D conversion of Compound 2B to the title lactone Compound 2D is accomplished via a novel, internally assisted saponification followed by a mild acid catalyzed lactonization. Both saponification and lactonization are effected without racemization. Thereafter, controlled crystallization of Compound 2D efficiently enriches the optical purity to greater than 99.5%.

This approach envisions a process of making Compounds of Formula 2D

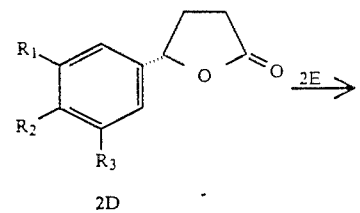

wherein:
$R^1$ is iodide, or bromide, or
$R^1$ is $S(O)_nR_a$ in which n is 0, 1 or 2 and $R_a$ is selected from the group consisting of
  (a) $C_{1-6}$alkyl,
  (b) $C_{1-6}$alkenyl,
  (c) $C_{2-6}$alkynyl,
  (d) substituted $C_{1-6}$alkyl wherein the substituted is selected from the group consisting of hydroxy, N-Cl-4alkylamino, and N,N-Cl-4di-alkylamino,
  (e) $C_{1-6}$alkoxy-$C_{1-6}$alkyl,
  (f) $C_{1-6}$alkylcarbonyl-$C_{1-6}$alkyl; and
$R_2$ is selected from the group consisting of
  (a) $C_{1-12}$alkoxy,
  (b) $C_{2-6}$alkenyloxy,
  (c) $C_{2-6}$alkynyloxy,
  (d) $C_{2-6}$(halo)x alkoxy wherein x is 1,2,3,4 or 5 and halo is chloro fluoro or bromo,
  (e) substituted $C_{1-6}$alkoxy wherein the substituent is hydroxy,
  (f) $C_{1-6}$alkoxy-$C_{1-6}$alkoxy,
  (g) $C_{1-6}$alkyl $S(O)_m$-$C_{1-6}$alkoxy in which m is 0, 1 or 2,
  (h) $C_{1-6}$alkyloxysulfonyl-$C_{1-6}$alkoxy,
  (i) $C_{1-6}$alkyl carbonyl-$C_{1-6}$alkoxy,
  (j) phenyl-$C_{1-6}$alkoxy,
  (k) azido-$C_{1-6}$alkoxy,
  (l) cyano-$C_{1-6}$alkoxy, (m) $C_{1-6}$alkylS(O)$_m$—$C_{1-6}$alkoxy, (n) N-substituted, or N,N-disubstituted amino-$C_{1-6}$alkyloxy wherein the substituents are each individually $C_{1-6}$alkyl;

$R_3$ is selected from the group consisting of (a) $C_{1-6}$alkoxy, (b) substituted $C_{1-6}$alkoxy wherein the substituted is selected from the group consisting of hydroxy, N-$C_{1-4}$alkylamnio, N,N-di$C_{1-4}$alkylamino, (c) —O—$C_{1-6}$alkyl—O—$R^{10}$, wherein $R^{10}$ is (1) —PO$_2$(OH)$^-$ M$^+$ wherein M$^+$ is a pharmaceutically acceptable cation, (2) —C(O) (CH$_2$)$_2$—CO$_2^-$M$^+$, or (3) —SO$_3^-$M$^+$, (d) $C_{1-6}$-alkylcarbonyl-$C_{1-6}$alkoxy, (e) $C_{1-6}$-alkoxyaminocarbonyloxy, (f) halophenyl $C_{1-6}$-alkoxy, and (g) $C_{1-6}$carboxyalkoxy, comprising:

(2A) Contacting, in the substantial absence of oxygen, and in the presence of a catalyst compound of formula 2F

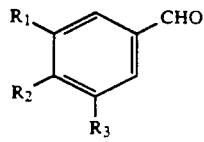
2F wherein $R_1$ is iodide or bromide, with an acrylate derivative of formula

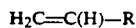

wherein R is CO$_2$Et, CO$_2$Me, CO$_2$CH$_2$Ph, CO$_2$CH$_2$CHCH$_2$, CO$_2$Ph, CO$_2$—t—C$_4$H$_9$ or CN, to yield a compound of formula 2A;

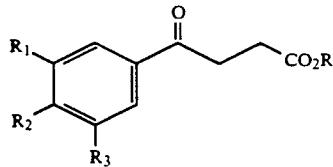
2A

Preferably, contacting step 2A is carried out in two stages. The first stage comprises degassing a solution of compound 2F in the first solvent, followed by addition of a catalytic amount of alkali metal cyanide to the solution of compound 2F in the first solvent. Degassing may conveniently be accomplished by bubbling nitrogen gas through the solution for 10 minutes under ambient conditions. The cyanide is then added and the reagents are stirred for about 10 to 100 minutes. 30 minutes under constant stirring has proven quite satisfactory.

While the first stage may be carried out at up to 100 atmospheres, this stage is preferably carried out at ambient pressure. Temperature can range from 20° to 30° C., but is preferably at about 25° C. The ratio of alkali metal cyanide to compound 2F is 0.1 to 0.3 moles per 100 moles, most preferably 0.25 mole.

Contacting step 2A is then completed by direct addition of the acrylate derivitive, preferably over a 50 to 60 minute period, at from 0° to 25° C.

For purposes of this specification, the first solvent includes, but is not limited to, such solvents as mono or di $C_{1-6}$ alkyl amide derivatives such as dimethylformamide (DMF); di-$C_{1-6}$ alkyl sulfoxide, such as methyl-sulfoxide or aqueous $C_{1-6}$ alcohol, such as ethanol, most preferably DMF. The alkali metal cyanide is a cyanide such as sodium, potassium or lithium cyanide, preferably sodium cyanide.

The acrylate derivitive, is preferably a sterically hindered acrylate, such as CO$_2$—t—C$_4$C$_9$. The selected acrylate is preferably added gradually over 1 hour to provide the desired γ-keto ester of formula 2A in a yield of approximately 80% (for R=CO$_2$—t—C$_4$H$_9$, 80%). Critical to reaction success was the discovery that oxygen exclusion is a requirement. In its presence, oxidative decomposition leading to by-products depress the yield significantly;

(2B) Contacting the compound of formula 2A in an etheral solvent with β-chlorodiisopinocampheyl borane to yield a compound of formula 2B

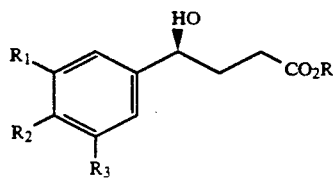
2B

For purposes of this specification, etheral solvents include, but are not limited to ethers such as diethyl ether di-n-butyl and diisopentyl ethers, anisole, cyclic esthers such as tetrahydropyran, 4-methyl-1,3-dioxane, dihydropyran, tetrahydrofurfuryl methyl ether, ethyl ether, furan and 2-ethoxytetrahydrofuran, most preferably tetrahydrofuran.

The reaction can be conducted at −25° to 25° C. preferably at 0° to 5° C. The reaction is allowed to proceed until essentially complete in about 1 to 100 hours, preferably 18 hours. While the pretreatment may be carried out at up to 100 atmospheres, the reaction is preferably carried out at ambient pressure. The γ-hydroxy butanoate derivative compound 2B is provided in typically 80–90% yields with an enantiomeric excess (ee) of 92%. Use of the (−)-chloroborane enantiomer provides the 4S-alcohol while the (+)-chloroborane enantiomer yields the 4R-alcohol. Thus both enantiomers of 2B are accessible by this invention. The reaction of γ-keto esters with this reducing agent is highly unprecedented as prior art indicates that β-keto-esters are not suitable substrates.

(2C) Contacting compound 2B in a medium containing alcohol in an etheral solvent with an alkali metal hydroxide to yield a compound of formula 2C.

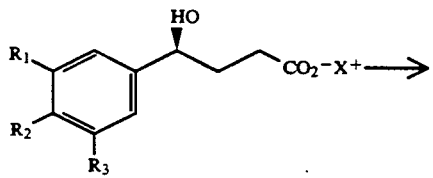
2C wherein X is an alkali metal selected from the group consisting of Sodium, Potassium and Lithium.

For purposes of this specification, alcohol includes, but is not limited to $C_{1-6}$ alkanol, preferably ethanol. As before, sodium hydroxide is the preferred alkali metal hydroxide. For purposes of this specification, etheral solvents include, but are not limited to ethers such as diethyl ether di-n-butyl and diisopentyl ethers, anisole, cyclic esthers such as tetrahydropyran, 4-methyl-1,3-dioxane, dihydropyran, tetrahydrofurfuryl methyl ether, ethyl ether, furan and 2-ethoxytetrahydrofuran, most preferably tetrahydrofuran. For complete saponification, the molar ratio of alkali metal hydroxide to compound 2C should be at least 1 to 1, preferably 1.5 to 1 or greater. The time, temperature and pressure of the reaction are not considered critical. The reaction can be conducted at −25° to 50° C., preferably at 25° C. The reaction is allowed to proceed until essentially complete in about 20 to 200 minutes, preferably 75 minutes. While the reaction may be carried out at up to 100 atmospheres, the reaction is preferably carried out at ambient pressure.

Highlighting this step is the intramolecular assistance provided by the γ-hydroxyl moiety in compound 2B which facilitates removal of the R-oxy group under basic conditions. Normally recommended acid catalyzed procedures for hydrolysis of the R ester would likely result in significant racemization of this substrate. Saponification yields compound 2C as a free acid salt, readily extractable into water and consequently easily separated from the neutral pinanyl by-products resulting from the chiral reduction step.

Thereafter the acid salt of compound 2C can be converted to the acid by any of the conventional means known in the art. Our preferred procedure is described in the Example and incorporates partial purification of the resulting acid.

(2D) Contacting the free acid of compound 2C in a second solvent with pyridinium para-toluene sulfonate to yield a compound of formula 2D.

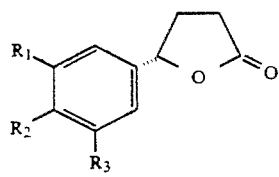

2D

For purposes of this specification the second solvent includes, but is not limited to, an etheral solvent, as defined above, or a $C_{6-10}$ linear, branched or cyclic hydrocarbon solvent. Toluene is preferred. The time, temperature and pressure of the reaction are not considered critical. The reaction can be conducted at 50° to 80° C., preferably at 70° C. The reaction is allowed to proceed until essentially complete in about 20 to 200 minutes, preferably 90 minutes. While the reaction may be carried out at up to 100 atmospheres, the reaction is preferably carried out at under ambient pressure in a nitrogen atmosphere.

Significantly, racemization does not occur, even with highly electron rich substrates.

The 80 to 95% optically pure product can be optically enriched to greater than 99.5% enantiomeric excess by controlled crystallization from ethyl acetate, isopropyl acetate, ethanol, methanol, or solvent mixtures of a hydrocarbon solvent such as hexanes, cyclohexane and esters such as ethyl acetate, isopropyl acetate or ethers such as methyl t-butyl ether. Preferably the optically enriched product is crystallized from an ethyl acetate/hexane mixture in a 1:6 ratio v/v at −10° C. to 20° C. This provides 99.5% ee pure compound 2D.

The following examples illustrate the present invention and as such are not to be considered as limiting the invention set forth in the claims appended thereto.

The starting materials are either known, described hereunder or described in U.S. Ser. No. 546,486 of same title, filed contemporaneously with this application which is hereby incorporated by reference.

EXAMPLE 1

Step A

4[3-Methoxy-4-n-propyloxy-5-(2'-t-butyldimethylsiloxyethylsulfonyl)phenyl]-4-butyrolactol

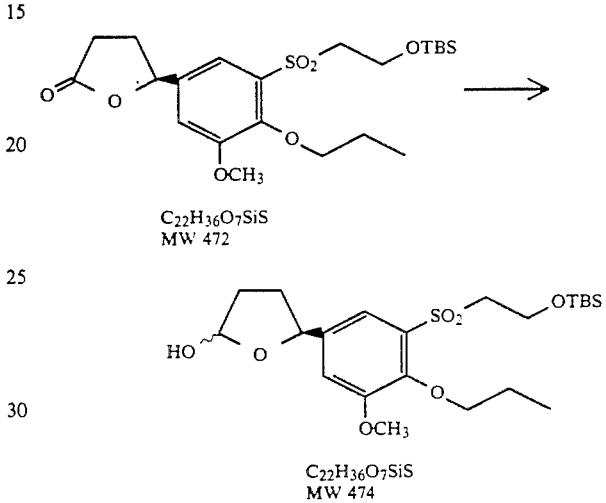

$C_{22}H_{36}O_7SiS$
MW 472

$C_{22}H_{36}O_7SiS$
MW 474

| Materials | Amt | Mols | MW |
|---|---|---|---|
| 4[3-Methoxy-4-n-propyloxy-5-(2'-t-butyldimethylsiloxyethylsulfonyl)phenyl]-4-butyrolactone | 1.607 Kg | 3.405 | 472 |
| Diisobutylaluminum hydride 1.5M in toluene | 3.5 L | 5.25 | 1.5M |
| Methanol (d = 0.791) | 1.5 L | 37.08 | 32 |
| Potassium sodium tartrate tetrahydrate | 12 L | | 281.2 |
| Ethyl Acetate | 12 L | | |
| Toluene | 13 L | | |

To a solution of the lactone (1.607 kg, 3.405 mole) in sieve dried toluene (13 L) at −72° C. is added a 1.5M toluene solution of diisobutylaluminum hydride (3.50 L, 5.25 mole) dropwise over 1.25 hours maintaining an internal temperature of <−65° C. The mixture is stirred at −70° C. for 1.0 hours.

The reaction is quenched through the slow addition of methanol (1.5 L) at −70° C. then the mixture is warmed to −20° C. Saturated Rochelle's salt (12 L) is added over 0.5 hours keeping the temperature <10° C. and the mixture then stirred at 5° C. for 1.5 hours, then the two phases separated. The aqueous layer is extracted with ethyl acetate (12 L). The organic phase is washed with DI water (2×8.0 L) and with saturated aqueous sodium chloride (10 L). The organic extracts are concentrated in vacuo to provide 1.799 Kg of the lactol as a light yellow oil. HPLC assay indicated this product to be 87 wt % pure (97% yield). The lactol is suitable for use without further purification.

Step B

5[3-Methoxy-4-n-propyloxy-5-(2'-t-butyldimethylsiloxyethylsulfonyl)phenyl]-1-(t-butyldimethylsiloxy)-butyrolactol

Step C

Preparation of 1-tert-butyldimethylsiloxy-2-((2-methoxy-2-propyloxy-5-(tetrahydro-5-(3,4,5-trimethoxyphenyl)-2-furanyl)-phenylsulfonyl-trans-(—)-ethane

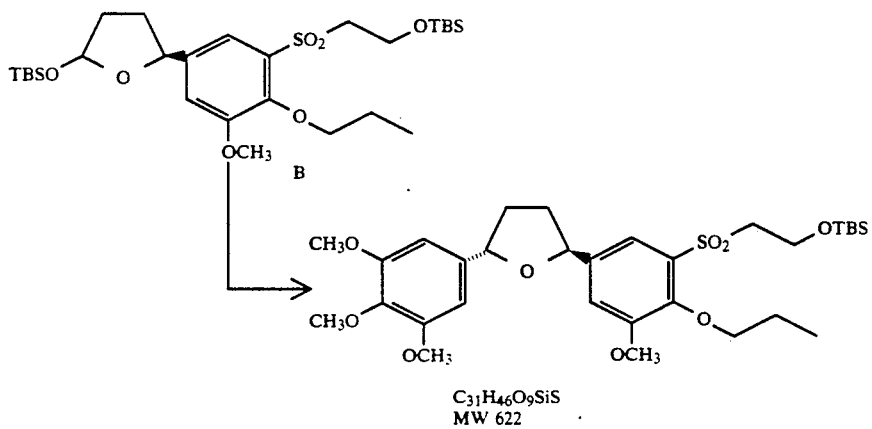

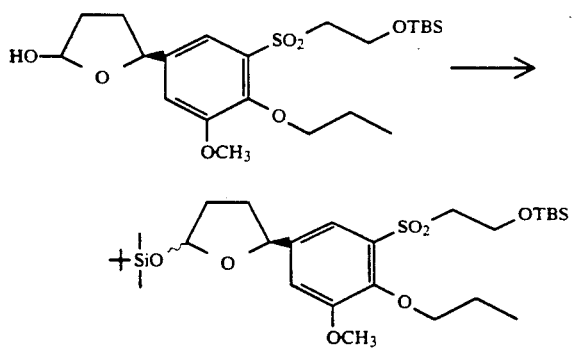

| Materials | Amt | Mole | MW |
|---|---|---|---|
| 5[3-Methoxy-4-n-propyloxy-5-(2'-t-butyldimethylsiloxyethylsulfonyl)phenyl]-1-(t-butyldimethylsiloxy)-1-butyrolactol | 1.522 Kg | 3.211 | 474 |
| Imidazole | 0.48 Kg | 7.059 | 68 |
| t-Butyldimethylsilylchloride | 0.53 Kg | 3.533 | 150 |
| Dimethylformamide | 3.0 L | | |

To a solution of the lactol (1.522 Kg, 3.211 mole) in sieve dried DMF at 25° C., under $N_2$, was added imidazole (0.48 Kg, 7.059 mole), followed by t-butyldimethylsilylchloride (0.53 Kg, 3.533 mole). The internal temperature rises to +34° C. within ½ hour, then cools to 25° C. Stir at 25° C., under $N_2$ for 3 hours. The reaction was diluted with EtOAc (20 liter), washed with $H_2O$ (3×10 L) followed by brine (10 L). The organics were concentrated to afford 2.170 Kg of a yellow oil. 300 MHz NMR is consistent for silyl hemiacetal.

HPLC assay indicated this product to be 87.5% pure (100% yield). This material is suitable for use without further purification.

| Materials | | |
|---|---|---|
| 5-[3-Methoxy-4-n-propyloxy-5-(2'-t-butyldimethylsiloxyethyl-sulfonyl)phenyl]-1-(t-butyldimethylsiloxy)-butyrolactol (B) | 0.829 Kg | 1.409 mole |
| TMS-Br | 0.232 L | 1.759 mole |
| $Li_2CuCl_4$/THF 0.5M | 0.060 L | 0.030 mole |
| 3,4,5-trimethoxyphenyl magnesium bromide (0.9M in THF) | 2.25 L | 2.025 mole |
| $CH_2Cl_2$ | 6.0 L | |
| Ethyl Acetate | 13 L | |

The silyl ether B (0.829 Kg, 1.409 mole) was dissolved in $CH_2Cl_2$, under $N_2$. The mixture was cooled to −60° C. and then neat trimethylsilylbromide (0.232 L, 1.759 mole) was added. The mixture was stirred at −60° C. for 1.5 hours. In a separate flask containing 3,4,5-trimethoxyphenylmagnesium bromide (0.9M, 2.5 L, 2.025 mole), at 0° C. under $N_2$ was added a THF solution of $Li_2CuCl_4$ (0.060 mL, 0.030 mole).

To the glycosyl bromide at −60° C. was transferred the solution of organometallic. After complete addition, the reaction was stirred at −60° C. for 1.0 hours. It was quenched at −60° C. by addition of 10 L of saturated $NH_4Cl/NH_4OH$ (10:1 v/v), and $H_2O$ (5 L). Allow to stir without external cooling for 0.5 hours. After separating the organic layer, the aqueous layer was extracted with EtOAc (10 L) and the combined organics were washed with brine (8 L). The resulting clear, homogeneous organic layer was concentrated to affor 1.178 Kg of a red oil. Analysis of the crude reaction mixture by HPLC assay showed 0.754 Kg (86%) of the title compound.

PREPARATION OF STARTING MATERIALS

EXAMPLE 2

Preparation of tert.-butyl 3[3-methoxy-4-n-[propyloxy-5-iodobenzoyl]propionate

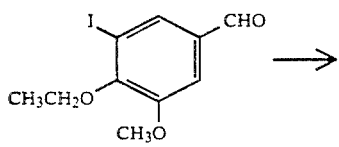

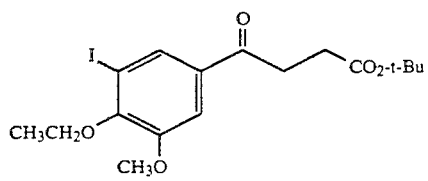

| Materials | Amt | Moles | MW |
|---|---|---|---|
| 3-Methoxy-4-n-propyloxy-5-iodo-benzaldehyde (0.47M soln. in DMF) | 100 mL | 0.0469 | 320 |
| Dimethyl formamide | 32 mL | | |
| Sodium cyanide | 0.574 g | 0.0117 | 49 |
| t-Butyl acrylate | 5.40 g | 0.0422 | 128 |
| Ethyl acetate | 150 mL | | |
| Saturated aq. NaCl | 65 mL | | |
| Saturated aq. NaHCO₃ | 75 mL | | |
| Water | 195 mL | | |

A 3-methoxy-4-n-propyloxy-5-iodobenzaldehyde solution in DMF (100 mL, 15 g, 0.0469 mole) (KF=640 μg/mL) is degassed by bubbling N₂ through the solution for 10 minutes. Sodium cyanide (0.574 g, 0.0117 mole) is added in one portion and the mixture is stirred for 30 minutes under N₂. The temperature rises from 24° C. to 28° C.

After a total age time of 45 minutes, the solution is cooled to 18° C. A solution of t-butyl acrylate (6.17 mL, 5.40 g, 0.0422 mol) in sieve-dried deoxygenated dimethylformamide (32 mL) (KF=170 μg/mL) is added over 50 minutes at 18° C.

The reaction is aged for 30 minutes after complete acrylate addition. Ethyl acetate (75 mL), distilled water (45 mL) and saturated aqueous sodium chloride (45 mL) are added to the reaction mixture and the layers are separated.

The aqueous phase is back extracted with ethyl acetate (75 mL). The combined organic extracts are washed with saturated aqueous sodium bicarbonate (75 mL), followed by 2×75 mL of distilled H₂O and 10 mL of saturated aqueous sodium chloride. The ethyl acetate layer is dried over sodium sulfate, filtered and concentrated in vacuo to give the desired ketoester in an 85% yield by HPLC assay.

EXAMPLE 3

Ethyl 3[3-methoxy-4-n-propyloxy-5-iodobenzoyl]propionate

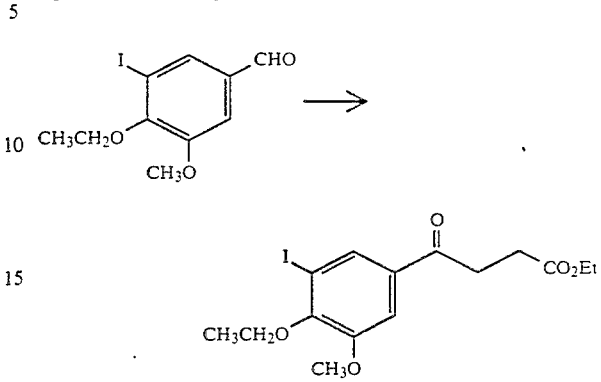

| Materials | Amt | Moles | MW |
|---|---|---|---|
| 3-Methoxy-4-n-propyloxy-5-iodo-benzaldehyde | 3.67 kg | 11.46 | 320.05 |
| Dimethyl formamide | 28.4 L | | |
| Sodium cyanide | 140.7 g | 2.88 | 49 |
| Ethyl acrylate | 1.15 k | 11.45 | 100 |
| Ethyl acetate | 36.0 L | | |

3-Methoxy-4-n-propyloxy-5-iodobenzaldehyde (4.021 kg, 3.67 kg/HPLC assay 11.46 mole) is dissolved in dry dimethylformamide (KF-420 μg/ml) (21.0 L) under N₂. Sodium cyanide (140.7 g, 2.88 mole) is added in one portion and the mixture stirred for 45 minutes under nitrogen. The temperature rises from 18° C. to 22° C. during the age.

After a total age time of 1.5 hours, the batch is cooled to 20° C. A solution of ethyl acrylate (1.234 L, 1.15 kg, 11.45 moles) in dry dimethylformamide (7.4 L) is added over 2¼ hours at 20°-23° C. [cooling as needed].

Ethyl acetate (17.9 L), cold distilled water (11.4 L) and saturated aqueous sodium chloride solution (11.4 L) are added to the reaction mixture with stirring and the phases separated. The organic phase is washed with saturated aqueous sodium chloride solution (11.4 L). The combined aqueous layers are back-extracted with ethyl acetate (17.6 L). The combined organic extracts are washed with 2×17.9 L of distilled water. An emulsion which may form in the final wash can be broken through addition of 2.7 L of saturated sodium chloride solution. The ethyl acetate layer is dried over anhydrous sodium sulfate, filtered and concentrated in vacuo to give 4.462 kg of the title compound as an oil.

EXAMPLE 4 tert-Butyl 4[3-methoxy-4-n-propyloxy-5-iodophenyl]-4S-hydroxybutyrate

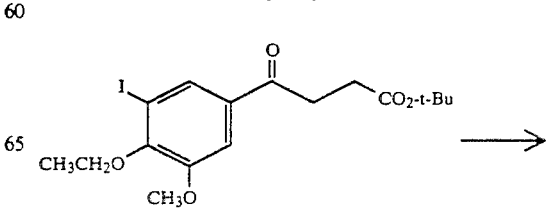

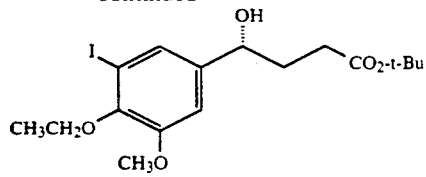

| Materials | Amt | Moles | MW |
|---|---|---|---|
| t-Butyl 3[3-methoxy-4-n-propyl-5-iodobenzoyl]propionate | 9.3 g | 0.0219 | 448 |
| (−)-β-Chlorodiisopinocampheylborane | 11.9 g | 0.0372 | 320 |
| Tetrahydrofuran | 20 mL | | |
| 30% Hydrogen Peroxide | 10 mL | | |
| Water | 100 mL | | |
| Ethyl acetate | 75 mL | | |
| Saturated aqueous sodium bicarbonate | 60 mL | | |
| Saturated aqueous sodium chloride | 30 mL | | |

(−)-β-Chlorodiisopinocampheylborane (11.9 g, 0.0372 mol) is dissolved in sieve-dried tetrahydrofuran (10 mL, KF=74 μg/mL) under nitrogen. The solution is cooled to 0°-5° C. in an ice bath. Meanwhile, a solution of crude t-butyl 3[3-methoxy-4-n-propyl-5-benzoyl]propionate (10.0 g, 9.3 g by HPLC assay, 0.0219 mol) in dry tetrahydrofuran (10 mL) is prepared. The solution is added dropwise at 0°-5° C. to the chiral reducing agent under nitrogen. The reaction is stirred at 0° C. and monitored by HPLC.

The reaction is quenched by dropwise addition of distilled water (7 mL) at 5°-10° C. 30% Hydrogen peroxide (10 mL) is slowly added maintaining the temperature at 10°-20° C. The mixture is added to distilled water (30 mL) and ethyl acetate (75 mL). The layers are separated and the organic phase is washed with 30 mL of distilled water, 2×30 mL of half-saturated aqueous sodium chloride. The organic phase is dried over anhydrous sodium sulfate, filtered and concentrated in vacuo to provide the title compound as a yellow oil (18.2 g).

EXAMPLE 5

Ethyl 4[3-methoxy-4-n-propyloxy-5-iodophenyl]-4S-hydroxybutyrate

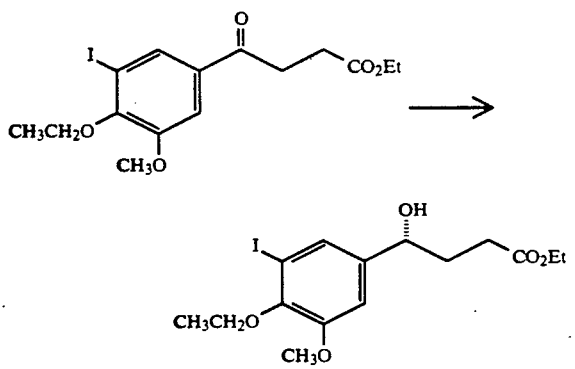

| Materials | Amt | Moles | MW |
|---|---|---|---|
| Ethyl 3[3-methoxy-4-n-propyl-5-benzoyl]-propionate | 1.39 kg | 3.31 | 420.05 |
| (−)β-Chlorodiisopinocamphenyl-borane | 1.9 kg | 5.92 | 320.76 |
| Tetrahydrofuran | 2.86 L | | |
| 30% Hydrogen peroxide | 960 ml | | |
| Ethyl acetate | 14.0 L. | | |
| Sodium bicarbonate | | | |

(−)-β-Chlorodiisopinocamphenylborane (1.7 kg, 5.3 moles) is dissolved in sieve-dried tetrahydrofuran (1.43 L, KF=335 μg/ml) under nitrogen at 25° C. The solution is cooled to 0°-5° C. in an ice/methanol bath. Meanwhile, a solution of crude ethyl 3[3-methoxy-4-n-propyloxy-5-iodobenzoyl] propionate (1.82 kg, 1.39 kg HPLC assay basis, 3.31 moles) in dry tetrahydrofuran (1.43 L) is prepared. Anhydrous sodium sulfate is used to assure dryness of the solution. The solution is filtered and added over 1.0 hour at 0°-5° C. to the chiral reducing agent under nitrogen. The batch is stirred overnight at 0°-5° C.

Additional chiral reducing agent (200 g, 0.629 mole) is charged at 0°-5° C. and the mixture aged for another 24 hours.

HPLC now shows 79.4% product and 0.5% s.m.; the estimated extent of reaction is now 99.7%.

The reaction is quenched with distilled water (477 ml) at 5°-10° C. over 40 minutes [dry ice/methanol cooling]. 30% Hydrogen peroxide (960 ml) is added over 1.25 hour at 15°-20° C. The mixture is added to a 10-gallon extractor containing distilled water (4.0 L) and ethyl acetate (11.4 L) with stirring. The reaction vessel is rinsed with distilled water (1.77 L) and ethyl acetate (2.0 L). The layers are separated and the organic phase is washed with 5.77 L of distilled water, 2×5.77 liters of 10% sodium bicarbonate solution and 2×5.77 liters of half-saturated sodium chloride solution. The batch was dried over anhydrous sodium sulfate, filtered and concentrated in vacuo to an oil. The residue is diluted with tetrahydrofuran (2 L) and again concentrated to give 3.32 kg of hydroxy-ester as an oil. This product is hydrolyzed without further purification.

EXAMPLE 6

4[3-Methoxy-4-n-propyloxy-5-iodophenyl]-4-hydroxybutyric acid

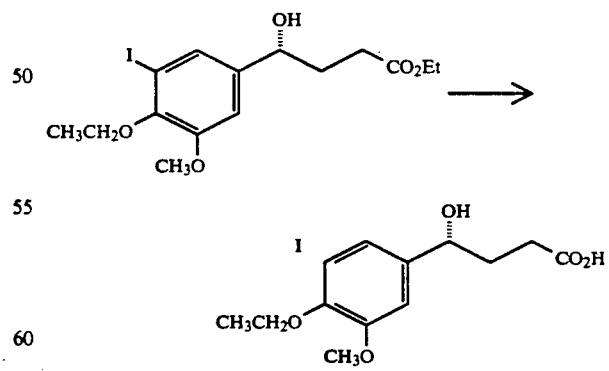

| Materials | Amt | Moles | MW |
|---|---|---|---|
| Ethyl 4[3-methoxy-4-n-propyloxy-5-iodophenyl]-4-hydroxybutyrate | 3.32 kg | 3.31 (theor) | 422.05 |
| Sodium hydroxide | 230 g | 5.75 | 40 |
| Tetrahydrofuran | 5.75 L | | |

| Materials | Amt | Moles | MW |
|---|---|---|---|
| Methyl-t-butyl ether | 58.0 L | | |
| Hydrochloric acid | 875 ml | 1.01 | 11.6M |

The crude hydroxyester (3.32 kg, 3.31 moles-theor.) is dissolved in tetrahydrofuran (5.75 L) and the solution is added to 1M sodium hydroxide solution (5.75 L). The batch is aged at 25° C. for 1.25 hours.

10% Aqueous sodium bicarbonate solution (3.83 L) then methyl t-butyl ether [MTBE] (11.5 L) are added. The layers are separated [aqueous pH=9.2] and the aqueous layer extracted with another 2×11.5 L of MTBE. The alkaline aqueous layer is acidified to pH=2.0 with 6N aqueous hydrochloric acid (1.75 l) and the γ-hydroxy acid product extracted into 2×11.5 L of MTBE. The organic phase is dried over anhydrous sodium sulfate, filtered and concentrated in vacuo to an oil. The residue is flushed with toluene (2.0 L) and again concentrated to give 1.35 kg of crude γ-hydroxy acid as an oil. This is used without purification in the lactonization step.

EXAMPLE 7

4[3-Methoxy-4-n-propyloxy-5-iodophenyl]-4S-butyrolactone

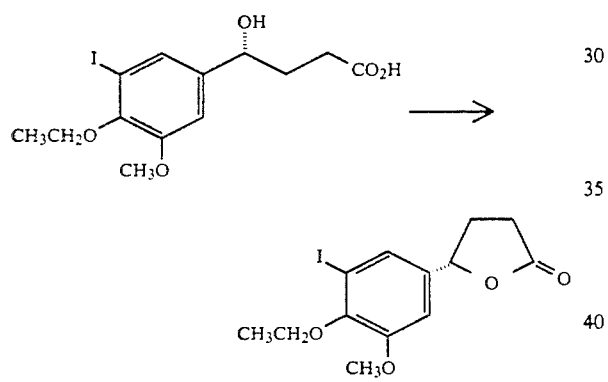

| Materials | Amt | Mole | MW |
|---|---|---|---|
| 4[3-Methoxy-4-n-propyloxy-5-iodophenyl]-4S-hydroxybutyric acid | 1.35 kg | 3.31 (theor) | 392 |
| Pyridinium-p-toluenesulfonate | 12.1 g | 0.048 | 251.3 |
| Toluene | 11. L | | |

The crude γ-hydroxyacid (1.35 Kg) is dissolved in toluene (11.5 L) and charged to a 50 L R.B. flask. Pyridinium-p-toluene-sulfonate [PPTS] (12.1 g, 0.048 mole) is added and the mixture heated to 70° C. under N₂. The reaction mixture is placed under vacuum [ca. 20 inches] and water is azeotropically removed. The batch is aged at 70° C. for 1.5 hours.

The mixture is concentrated in vacuo to a total volume of 4.0 L and transferred to a large Buchi Rotovapor, concentrated to an oil, flushed with 2×2.0 liters of ethyl acetate and again concentrated to an oil which solidifies as a waxy solid. This residue is dissolved in 900 ml of ethyl acetate, filtered to remove a small amount of insoluble material (1.2 g) and the solids washed with 250 ml of hexanes. Hexanes (2.0 L) are added while stirring, and seeded with 100 mg of lactone. Additional hexanes (3.07 L) are added and the batch is stirred overnight at 0°-5° C. to complete the crystallization. The solids are filtered, washed with 3×260 ml of cold hexanes/ethyl acetate [4/1] and dried in vacuo at 25° C., to yield, 947.6 g of an off-white solid. This material is of acceptable quality for continued processing.

NMR [4 mg lactone+40 mg (S)-(+)-2,2,2,-trifluoro-1-(9-anthryl) ethanol in CD₂Cl₂] showed >99.5% ee.

EXAMPLE 8

Lactone Recrystallization

In cases in which the initially isolated lactone is not suitable for continued processing [<99.5% ee]. The following recrystallization procedure is employed.

| Materials | |
|---|---|
| 4[3-Methoxy-4-n-propyloxy-5-iodophenyl]-4S-butyrolactone | 1.656 kg |
| Ethyl acetate | 1.9 L |
| Hexanes | 7.2 L |

Crude lactone [1.656 kg] is dissolved in ethyl acetate (1.65 L) at 45° C. and filtered from insolubles [ca. 5 g]. The insolubles are washed with 250 ml of ethyl acetate. Hexanes (1.8 L) are added to the combined filtrate plus washes and seeded with 100 mg of lactone. Additional hexanes (5.46 L) are added and the batch allowed to crystallize for one half hour at 25° C. Crystallization is completed by aging overnight in the cold room. The solids are filtered, washed with 3×500 ml of cold hexanes/ethyl acetate [4/1] and dried in vacuo at 25° C. to yield 1.377 kg [83.2%].

NMR [4 mg lactone+40 mg (S)-(+)-2,2,2,-trifluoro-1(9-anthryl)ethanol in CD₂Cl₂] showed >99.5% ee; HPLC (wt. %) was 98.9%.

EXAMPLE 9

4[3-Methoxy-4-n-propyloxy-5-iodophenyl]-4R-butyrolactone

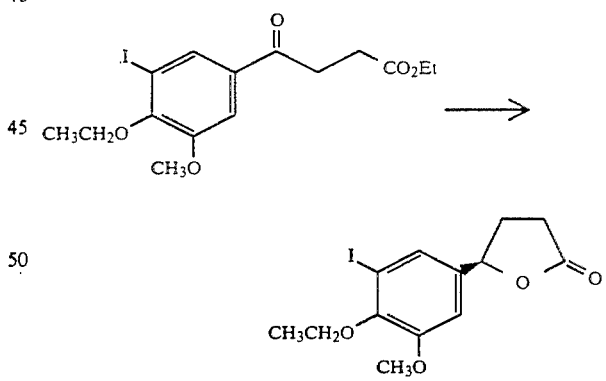

| Materials | Amt | Moles | MW |
|---|---|---|---|
| Ethyl 3[3-methoxy-4-n-propyl-5-iodo benzoyl]-propionate | 30.08 g | 0.073 | 420.05 |
| (+)β-chlorodiisopinocampheylborane | 38.56 g | 0.121 | 320.76 |
| Tetrahydrofuran | 125 ml | | |

A solution of (30.80 g, 73 mmol) of keto-ester in 25 ml of THF was added dropwise to a solution of (+)β-chlorodiisopinocampheylborane (32.5 g, 0.102 mole) in 100 ml of THF at 0° C. After 15 hours at 0°-5° an additional 6.0 g (0.019 g) of reducing agent was added and the reaction continued for an additional 27 hours. The reaction was quenched by dropwise addition of 20 ml of water followed by slow addition of 50 ml of 30% hydrogen peroxide over 30 minutes keeping the temperature <15° C. An additional 50 ml of water was added and the mixture was extracted with 400 ml of ethyl acetate. The organics were washed with water and saturated sodium bicarbonate, dried over sodium sulfate and concentrated in vacuo. The crude mixture was stirred at room temperature in 500 ml of THF and 110 ml of 1M sodium hydroxide for 1 hour. The mixture was diluted with 200 ml of saturated sodium bicarbonate and washed with 200 ml of diethyl ether. The aqueous phase was acidified with 6M HCl to pH 3 and extracted with diethyl ether. The organic layer was dried over sodium sulfate and concentrated in vacuo to yield 18.37 g of hydroxy acid. The crude hydroxy-acid was dissolved in 250 ml of toluene and 0.179 of pyridinium p-toluenesulfonic acid was added. The mixture was heated to 60° C. for 1 hour and concentrated in vacuo to a light yellow solid. Crystallization of the solid from ethyl acetate:hexane yielded 11.5 g of the 4R-butyrolactone which was >99% optically pure as determined by NMR using (S)(+)2,2,2,-trifluoro-1-(9-anthryl)ethanol as a chiral solvating agent.

EXAMPLE 10

4-[3-Methoxy-4-n-propyl-5-(2'-hydroxyethylthio)-phenyl]-4-butyrolactone

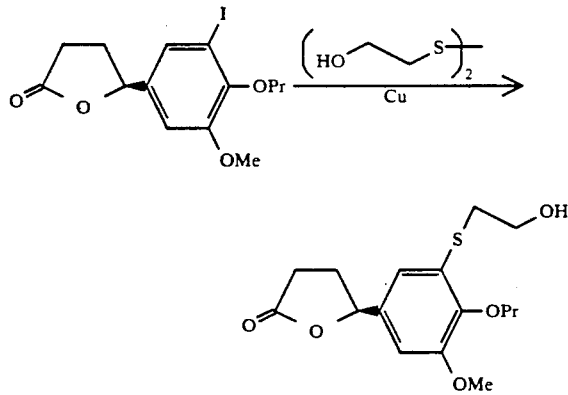

| Materials | Amount | Moles | MW |
|---|---|---|---|
| 4-[3-Methyoxy-4-n-propyl-5-idophenyl]-4-butyrolactone | 2.0 g | 5.33 mmol | 376.0 |
| Copper Powder (99%) | 0.51 g | 7.99 mmol | 63.5 |
| 2-Hydroxyethyl disulfide (95%) | 0.66 g | 4.26 mmol | 154.2 |
| Dimethylformamide | 15 ml | | |
| Ethyl acetate | 65 ml | | |

Iodolactone (2.0 g, 5.33 mmol) is dissolved in dimethylformamide (15 ml KF<200 μg/ml) at ambient temperature. Copper powder (0.51 g, 7.995 mmol) and then 2-hydroxyethyl disulfide (0.66 g, 4.264 mmol) is added to the solution. The mixture is heated to 108° C. for 22 hours. HPLC analysis [C-8, acetonitrile:water:phosphoric acid 60:40:0.1, 254 nm] shows no starting iodide and 3-5% formate ester byproduct.

Iodolactone: retention times=8.8 min.
Formate ester: retention times=5.0 min.
Sulfide: retention times=3.2 min.

The mixture is cooled to ambient temperature and 40 mL of ethyl acetate is added. The solution is stirred for 15 minutes and filtered through a celite pad. The addition of ethyl acetate prior to filtration greatly improves phase separation. The cake is washed with 25 ml of ethyl acetate. The combined organic extracts are washed with 3×40 ml of an ammonium chloride:ammonium hydroxide solution, followed by 40 ml of water. The ammonium chloride:ammonium hydroxide solution is prepared by adding approximately 65 ml of ammonium hydroxide solution (30%) to 300 ml of saturated aqueous ammonium chloride to a pH of 9.0. A pH range of 8.5-10.0 for this work has been determined to be satisfactory although pH 9.0 is favorable.

The organic extract is concentrated in vacuo to a volume of 4 ml. The solution is diluted with 2×20 ml of acetonitrile and reconcentrated to ~4 mL. The acetonitrile solution is used directly for the next step.

HPLC assay typically shows an 85–90% yield. $^1$H-NMR (300 MHz, CDCl$_3$) δ6.89 (d, J=1.8 Hz, 1H), 6.76 (d, J=1.8 Hz, 1H), 5.40 (dd, J=6.0, 8.2 Hz, 1H), 3.95 (t, J=6.8 Hz, 2H), 3.83 (s, 3H), 3.66 (q, J=6.0 Hz, 2H), 3.04 (t, J=5.9 Hz, 2H), 2.69–2.59 (m, 4H), 2.20–2.13 (m, 1H), 1.81 (sextet, J=7.1 Hz, 2H), 1.03 (t, J=7.4 Hz, 3H).

$^{13}$C-NMR (300 MHz, CDCl$_3$) δ176.8, 153.3, 147.5, 135.5, 129.8, 119.6, 108.4, 80.9, 75.2, 60.3, 56.1, 36.5, 31.0, 29.1, 23.5, 10.5.

EXAMPLE 11

4-[3-Methoxy-4-n-propyl-5-(2'-hydroxyethylsulfonyl)-phenyl]-4-butyrolactone

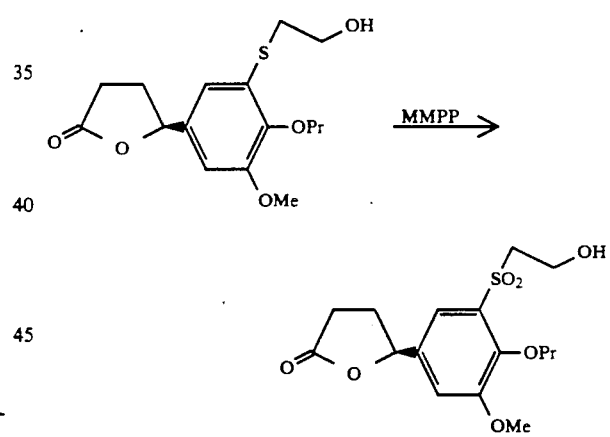

| Materials | Amount | Moles | MW |
|---|---|---|---|
| 4-[3-Methoxy-4-n-propyl-5-(2'-hydroxyethylsulfonyl)phenyl]-4-butyrolactone | 5.00 g | 15.3 mmol | 326.0 |
| Monoperoxyphthalic acid magnesium salt | 13.66 g | 27.6 mmol | 494.6 |
| Acetonitrile | 27 ml | | |
| Water | 40 ml | | |
| Saturated NaHCO$_3$ | 195 ml | | |
| 5% NaCl | 50 ml | | |
| Ethyl Acetate | 110 ml | | |
| DMF | 100 ml | | |

Monoperoxyphthalic acid magnesium salt (13.66 g, 27.6 mmol) was suspended in 40 ml of water at ambient temperature. A solution of sulfide (5.0 g, 15.3 mmol) in 27 ml of acetonitrile was added dropwise over 15 minutes keeping the temperature at <30° C. The mixture was then heated to 50° C. for 2 hours. HPLC analysis [C-8 acetonitrile:water:phosphoric acid 30:70:0.1, 10 minute gradient to 80:20:0.1, 254 nm] shows no sulfide or sulfoxide remaining.

Sulfide RT=9.9 min.
Sulfoxide RT=5.5 min.
Sulfone RT=7.7 min.

After cooling to room temperature 65 mL of saturated sodium bicarbonate was added over 5 minutes (gas evolution and the mixture was extracted with 55 ml of ethyl acetate. The aqueous layer was back extracted with 55 ml of ethyl acetate and the combined organics were washed with saturated sodium bicarbonate (2×65 ml) and 5% aqueous sodium chloride (50 mL). The organic extracts were concentrated in vacuo to a volume of 20 ml. DMF (100 ml) was added and then concentrated in vacuo to 20 ml. The solution is used for the next step. HPLC typically shows 95% yield.

$^1$H-NMR (300 MHz, CDCl$_3$) δ7.43 (d, J=1.8 Hz, 1H), 7.20 (d, J=1.9 Hz, 1H), 550 (dd, J=6.0, 8.7 Hz, 1H), 4.12 (m, 2H), 3.96 (t, J=5.2 Hz, 2H), 3.92 (s, 3H), 3.67–3.63 (m, 2H), 2.79–2.66 (m, 4H), 2.23–2.10 (m, 1H), 1.86 (sextet, J=7.2 Hz, 2H), 1.03 (t, J=7.4 Hz, 3H).

$^{13}$C NMR (300 MHz, CDCl$_3$) δ176.3, 154.1, 146.8, 135.6, 133.1, 117.4, 114.7, 80.2, 76.5, 57.5, 56.5, 30.9, 29.1, 23.2, 10.3.

EXAMPLE 12

4-[3-Methoxy-4-n-propyloxy-5-(2′-t-butyl-dimethyl-siloxyethylsulfonyl)phenyl]-4-butyrolactone

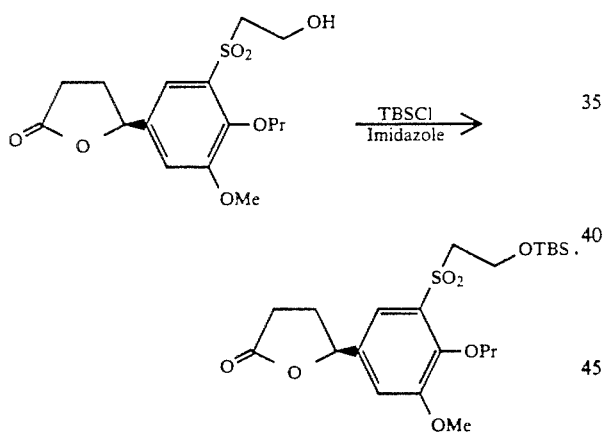

| Materials | Amount | Moles | MW |
|---|---|---|---|
| 4-[3-Methoxy-4-n-propyloxy-5-(2′-hydroxyethylsulfonyl)phenyl]-4-butyrolactone | 3.0 g | 8.38 mmol | 358 |
| Imidazole | 0.85 g | 12.57 mmol | 68 |
| t-butyldimethylsilyl-chloride | 1.39 g | 9.2 mmol | 150.7 |
| DMF | 3 ml | | |
| Ethyl Acetate | 18 ml | | |
| Water | 25 ml | | |
| 5% Aqueous NaCl | 50 ml | | |
| Toluene | 50 ml | | |

Imidazole (0.85 g, 12.57 mmol) was added to a solution of sulfone (3.0 g, 8.38 mmol) in 6 ml of DMF (KF+278 μg/ml) at room temperature (25° C.). A solution of t-butyldimethylsilylchloride (1.39 g, 9.2 mmol) in 3 ml of sieve dried DMF was added over 10 minutes keeping temperature ≦30° C. The mixture was stirred at 25° C. for 2 hours and the reaction followed by HPLC. HPLC assay [CH$_3$CN:H$_2$O:phosphoric acid 50:50:0.1 gradient to 80:20:0.1 over 8 minutes; C-8, 294 nm].

Alcohol RT=3.0 min.
Silyl ether RT=14.1 min.

Ethyl acetate (38 ml) was added and the mixture was washed with 25 ml water and then 2×25 ml with 5% aqueous sodium chloride. The organic extracts were concentrated in vacuo to a volume of 10 ml. Toluene (50 ml) was added and the solution was concentrated to a volume of 10 ml and checked by NMR for ethyl acetate (typically <5% EtOAc). HPLC assay typically shows 95% yield.

$^1$H-NMR (300 MHz, CDCl$_3$) δ7.38 (d, J=1.9 Hz, 1H), 7.15 (d, J=1.9 Hz, 1H), 5.46 (dd, J=5.8, 8.6 Hz, 1H), 4.10 (m, 2H), 3.95 (t, J=6.1 Hz, 2H), 3.89 (s, 3H), 3.72–3.57 (m, 2H), 2.67–2.61 (m, 3H), 2.20–2.10 (m, 1H), 1.86 (sextet, J=7.2 Hz, 3H), 1.03 (t, J=7.4 Hz, 3H), 0.73 (s, 9H), −0.092 (s, 3H), −0.097 (s, 3H).

$^{13}$C-NMR (300 MHz, CDCl$_3$) δ176.4, 154.0, 146.9, 135.1, 134.5, 117.2, 114.3, 80.4, 76.1, 57.6, 57.1, 56.4, 30.9, 29.1, 25.6, 23.2, 18.0, 10.3, −5.7.

What is claimed is:

1. A process of making a compound of Formula D:

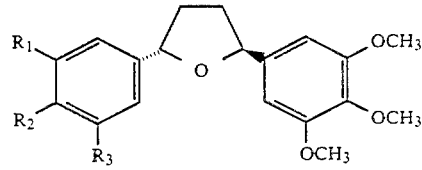

wherein:

R$^1$ is iodide, or bromide, or
R$^1$ is S(O)$_n$R$_a$ in which n is 0,1 or 2 and R$_a$ is selected from the group consisting of
(a) C$_{1-6}$alkyl,
(b) C$_{1-6}$alkenyl,
(c) C$_{2-6}$alkynyl,
(d) substituted C$_{1-6}$alkyl wherein the substituent is selected from the group consisting of hydroxy, protected hydroxy, N-Cl-4-alkylamino, and N,N-Cl-4di-alkylamino,
(e) C$_{1-6}$alkoxy-C$_{1-6}$alkyl,
(f) C$_{1-6}$alkylcarbonyl-C$_{1-6}$alkyl;

R$_2$ is
(a) C$_{1-3}$alkoxy, or
(b) substituted C$_{1-3}$alkoxy wherein the substituent is hydroxy or protected hydroxy; and R$_3$ is selected from the group consisting of
(a) C$_{1-3}$alkyloxy,
(b) substituted C$_{1-3}$alkoxy wherein the substituent is selected from the group consisting of hydroxy, protected hydroxy, and
(c) —O—C$_{1-3}$alkyl—O—R$^{10}$, wherein R$^{10}$ is —PO$_2$(OH)$^-$M$^+$ wherein M$^+$ is a pharmaceutically acceptable cation;

comprising:
contacting of Compound C,

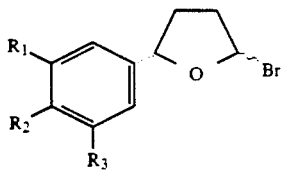

wherein the hydroxyl and amino groups of $R_1$, $R_2$ and $R_3$ are protected, said Compound C contacting with an organo metallic reagent species of the formula:

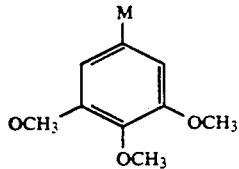

wherein M is selected from the group consisting of
(a) copper,
(b) magnesium,
(c) aluminum,
(d) lithium, and
(e) zinc,
in an etheral solvent to yield a compound of formula D:

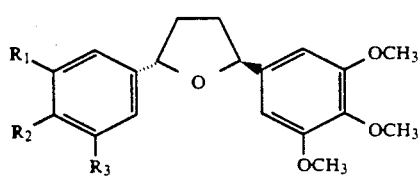

2. A process according to claim 1 wherein the etheral solvent is selected from the group consisting of, diethyl ether, di-n-butyl and diisopentyl ethers, anisole, tetrahydropyran, 4-methyl-1,3-dioxane, tetrahydrofurfuryl methyl ether, furan, tetrahydrofuran, dimethoxyethane, and diethoxymethane.

3. A process according to claim 2 wherein the etheral solvent is tetrahydrofuran and M is copper.

4. A process according to claim 3 wherein $R^1$ is $S(O)_nR_a$ in which n is 0,1 or 2 and $R_a$ is selected from the group consisting of
(a) $C_{1-6}$alkyl,
(b) protected hydroxy-$C_{1-6}$alkyl, and
(c) $C_{1-6}$alkyl-carbonyl-$C_{1-6}$alkyl.

5. A process according to claim 4 wherein
$R^1$ is $S(O)_2R_a$ wherein
$R_a$ is protected 2-hydroxyethyl, 2-oxopropyl or protected 2-hydroxypropyl,
$R_2$ is n-propoxy; and
$R_3$ is methoxy, 3-phosphopropoxy or protected 3-hydroxypropoxy.

6. A process according to claim 1 where the compound of formula D is
(−)-(2S,5S)-2-(3(2-hydroxyethylsulfonyl)-4-(n-propoxy)-5-methoxyphenyl)-5-(3,4,5-trimethoxyphenyl)tetrahydrofuran.

7. A process according to claim 1 further comprising contacting of Compound B

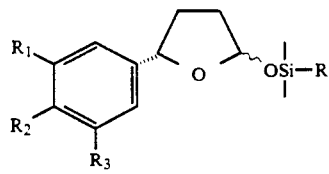

wherein R is $C_{1-6}$ alkyl;
with a silyl bromide in an etheral or halo carbon solvent to yield a glycosyl bromide Compound C;

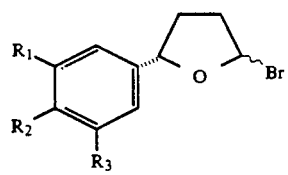

wherein the hydroxyl groups of substituent $R_1$, $R_2$ and $R_3$ are protected.

8. A process according to claim 7 wherein the third solvent is selected from the group consisting of mono or di halo $C_{1-4}$alkyl, diethyl ether, di-n-butyl and diisopentyl ethers, anisole, tetrahydorpyran, 4-methyl-1,3-dioxane, tetrahydrofurfuryl methyl ether, furan, tetrahydrofuran, methylene chloride, dimethoxyethane, diethoxymethane.

9. A process according to claim 8 wherein the silyl bromide is $C_{1-6}$ alkylsilyl bromide.

10. A process according to claim 9 wherein the solvent is methylene chloride and the silyl bromide is trimethylsilyl bromide.

11. A compound selected from the group consisting of

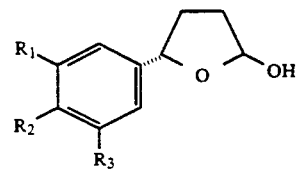

compund A' wherein:
$R^1$ is iodide, or bromide, or
$R^1$ is $S(O)_nR_a$ in which n is 0, 1 or 2 and $R_a$ is selected from the group consisting of
(a) $C_{1-6}$alkyl,
(b) $C_{2-6}$alkenyl,
(c) $C_{2-6}$alkynyl,
(d) substituted $C_{1-6}$alkyl wherein the substituent is selected from the group consisting of hydroxy, protected hydroxy, N-Cl-4alkylamino, and N,N-Cl-4di-alkylamino,
(e) $C_{1-6}$alkoxy-$C_{1-6}$alkyl,
(f) $C_{1-6}$alkylcarbonyl-$C_{1-6}$alkyl; and
$R_2$ is selected from the group consisting of
(a) $C_{1-3}$alkoxy, or
(b) substituted $C_{1-6}$alkoxy wherein the substituent is hydroxy or protected hydroxy; and
$R_3$ is selected from the group consisting of
(a) $C_{1-3}$alkoxy, (b) substituted $C_{1-6}$alkoxy wherein the substituent is hydroxy, and (c) $-O-C_{1-6}$alkyl$-O-R^{10}$, wherein $R^{10}$ is $-PO_2(OH)^- M^+$ wherein $M^+$ is a pharmaceutically acceptable cation;

compound B

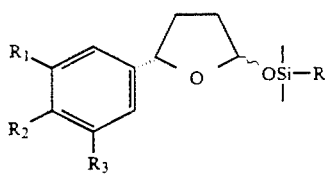

wherein R is $C_{1-6}$ alkyl; and, compound C

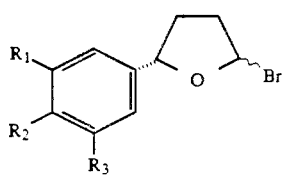

with the proviso that the hydroxyl groups of compound C are protected wherein $R_1$, $R_2$ and $R_3$ of compounds B and C are defined as herein above.

12. Compound C according to claim 11

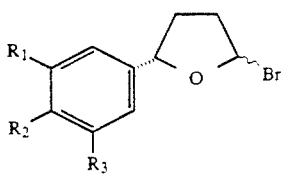

13. Compound C according to claim 11 wherein $R^1$ is $S(O)_nR_a$ in which n is 0, 1 or 2 and $R_a$ is selected from the group consisting of (a) $C_{1-6}$alkyl, (b) protected hydroxy-$C_{1-6}$alkyl, and (c) $C_{1-6}$alkyl-carbonyl-$C_{1-6}$alkyl;

(d) 2-t-butyldimethylsiloxy ethyl.

14. Compound C according to claim 13 wherein $R^1$ is $S(O)_2R_a$ wherein $R_a$ is protected 2-hydroxyethyl, 2-oxopropyl, 2-t-butyldimethyl siloxyethyl or protected 2-hydroxypropyl, $R_2$ is n-propoxy; and $R_3$ is methoxy, 3-phosphopropoxy or protected 3-hydroxypropoxy.

15. Compound B according to claim 11 wherein $R^1$ is $S(O)_nR_a$ in which n is 0, 1 or 2 and $R_a$ is selected from the group consisting of (a) $C_{1-6}$alkyl, (b) protected hydroxy-$C_{1-6}$alkyl, and (c) $C_{1-6}$alkyl-carbonyl-$C_{1-6}$alkyl.

16. A compound according to claim 15 wherein $R^1$ is $S(O)_2R_a$ wherein $R_a$ is protected 2-hydroxyethyl, 2-oxopropyl or protected 2-hydroxypropyl, $R_2$ is n-propoxy; and $R_3$ is methoxy, 3-phosphopropoxy or protected 3-hydroxypropoxy.

17. A process according to claim 1 wherein the compound of Formula D is
(−)-(2S,5S)-2-(3-(2-oxopropylsulfonyl)-4-(n-propoxy)-5-(3-phosphopropoxy)phenyl-5-(3,4,5-trimethoxyphenyl)tetrahydrofuran.

18. A process according to claim 1 wherein the compound of Formula D is
(−)-(2S,5S)-2-(3-(2-oxopropylsulfonyl)-4-(n-propoxy)-5-(3-hydroxypropoxy)phenyl-5-(3,4,5-trimethoxyphenyl)tetrahydrofuran.

19. A process according to claim 1 wherein the compound of Formula D is
(−)-(2S,5S)-2-(3-(2-hydroxyopropylsulfonyl)-4-(n-propoxy)-5-(3-hydroxypropoxy)phenyl-5-(3,4,5-trimethoxyphenyl)tetrahydrofuran.

* * * * *